United States Patent
Sullivan

(10) Patent No.: US 7,157,056 B2
(45) Date of Patent: Jan. 2, 2007

(54) SAMPLE INTRODUCTION DEVICE

(75) Inventor: Kevin J. Sullivan, Medfield, MA (US)

(73) Assignee: Bayer Corporation, E. Walpole, MA (US)

( * ) Notice: Subject to any disclaimer, the term of this patent is extended or adjusted under 35 U.S.C. 154(b) by 691 days.

(21) Appl. No.: 10/238,946

(22) Filed: Sep. 10, 2002

(65) Prior Publication Data

US 2004/0047768 A1    Mar. 11, 2004

Related U.S. Application Data

(63) Continuation of application No. 09/310,840, filed on May 12, 1999, now Pat. No. 6,446,516.

(51) Int. Cl.
*B01L 3/02* (2006.01)

(52) U.S. Cl. .................. 422/100; 73/64.56; 73/61.59; 73/61.55

(58) Field of Classification Search ............... 422/100; 73/64.56, 61.59, 61.55
See application file for complete search history.

(56) References Cited

U.S. PATENT DOCUMENTS

| | | | |
|---|---|---|---|
| 2,761,417 A | 9/1956 | Russell et al. | |
| 3,872,730 A | 3/1975 | Ringrose et al. | |
| 3,992,158 A | 11/1976 | Przybylowicz et al. | |
| 4,042,335 A | 8/1977 | Clement | |
| 4,356,149 A | 10/1982 | Kitajima et al. | |
| 4,478,095 A | 10/1984 | Bradley et al. | |
| 4,645,744 A | 2/1987 | Charlton et al. | |
| 4,649,123 A | 3/1987 | Charlton et al. | |
| 4,670,218 A | 6/1987 | Gantzer et al. | |
| 4,689,309 A | 8/1987 | Jones | |
| 4,734,375 A | 3/1988 | Charlton | |
| 4,781,890 A | 11/1988 | Arai et al. | |
| 4,895,704 A | 1/1990 | Arai et al. | |
| 4,999,307 A | 3/1991 | Oakley et al. | |
| 5,078,970 A * | 1/1992 | Teodorescu et al. | ........ 422/100 |
| 5,132,088 A | 7/1992 | Wakatake | |
| 5,163,582 A | 11/1992 | Godolphin et al. | |
| 5,279,796 A | 1/1994 | Parker et al. | |

(Continued)

FOREIGN PATENT DOCUMENTS

EP    0119861    11/1987

(Continued)

*Primary Examiner*—Jill Warden
*Assistant Examiner*—Natalia Levkovich
(74) *Attorney, Agent, or Firm*—Sampson & Associates P.C.

(57) ABSTRACT

A sample introduction device is provided that is particularly useful in the critical care environment for the anaerobic withdrawal of small volumes of arterial blood from a sample collection syringe and introduction thereof into a sample chamber of a sensor for analysis. The sample introduction device includes a Luer fitting adapted to mate an outlet of the container in a concentric orientation with an input aperture of the sample chamber. A tubular probe is adapted for concentric placement with both the outlet and inlet aperture, with a first end thereof extending into the syringe and a second end adapted for attachment to an air supply. The probe has a predetermined diameter sufficient to provide an annular clearance between the probe and each of the outlet and inlet aperture. A predetermined volume of air is injected through the probe into the container to displace a predetermined volume of sample therefrom, through the annular clearance into the sample chamber. Injecting air into the syringe through the probe to displace the sample therefrom, rather than drawing the sample into the probe, advantageously reduces or eliminates the need for washing the interior of the probe to relatively reduce the use of wash reagents.

11 Claims, 3 Drawing Sheets

U.S. PATENT DOCUMENTS

| | | |
|---|---|---|
| 5,387,525 A | 2/1995 | Munkholm |
| 5,395,347 A | 3/1995 | Blecher et al. |
| 5,462,858 A | 10/1995 | Bale Oenick et al. |
| 5,464,777 A | 11/1995 | Yip |
| 5,506,148 A | 4/1996 | Munkholm |
| 5,520,883 A | 5/1996 | Charlton et al. |
| 5,555,920 A * | 9/1996 | Godolphin et al. ......... 141/329 |

FOREIGN PATENT DOCUMENTS

| | | | |
|---|---|---|---|
| EP | 0 339 429 | * | 11/1989 |
| EP | 0339429 | | 11/1989 |
| EP | 0287328 | | 10/1993 |
| EP | 0287327 | | 7/1994 |
| GB | 1405782 | | 9/1975 |
| WO | WO95/26501 | | 10/1995 |
| WO | 97/36681 | | 10/1997 |
| WO | WO 99/38001 | * | 7/1999 |

* cited by examiner

SAMPLE INTRODUCTION DEVICE

This application is a Continuation of U.S. patent application Ser. No. 09/310,840, entitled Sample Introduction Device, filed on May 12, 1999 and issued as U.S. Pat. No. 6,446,516 on Sep. 10, 2002.

BACKGROUND OF THE INVENTION

1. Field of the Invention

This invention relates to sample handling devices, and more particularly to a device for introducing samples into sample chambers of a test instrument.

2. Background Information

Chemical analysis of liquids, including biological liquids such as blood, plasma or urine is often desirable or necessary. Sensors that utilize various analytical elements to facilitate liquid analysis are known. These elements have often included components which specifically react to a substance or characteristic under analysis, termed analyte herein. These components, upon contacting a liquid sample containing the analyte, effect formation of a colored or fluorescent material or another detectable response to the presence of the analyte.

In this regard, analytical elements such as disclosed in commonly assigned U.S. patent application Ser. No. 08/617,714 (hereinafter, the '714 Patent Application) have been provided. Analytical elements of this type are adapted for use within a sample chamber of an optical sensor assembly. In operation, a fluid sample of unknown analyte content (an "unknown sample") is tested by introducing the sample into the sample chamber where it contacts the analytical element. Any change in the optical characteristics of the analytical element are observed to thus determine characteristics of the analyte of interest in the sample. An example of a sensor assembly of this type is disclosed in commonly assigned U.S. patent application Ser. No. 09/010,096, entitled "OPTICAL SENSOR AND METHOD OF OPERATION" (hereinafter referred to as the "OPTICAL SENSOR" patent application) which is hereby incorporated by reference in its entirety, herein. The sample chambers of this and similar types of sensor assemblies are generally incorporated in multiple use clinical instrumentation which utilize a sample introduction device, including an aspiration probe, to withdraw a sample, such as blood or other fluid, from a syringe or the like and transfer the sample into the sample chamber. An example of instrumentation that utilizes an aspiration probe to withdraw a sample is disclosed in commonly assigned U.S. patent application Ser. No. 60/006,741, entitled "MULTIFUNCTION VALVE" filed on Nov. 2, 1995.

In this type of instrumentation, once the tip of the aspiration probe is immersed within the syringe, a suction pump draws blood through the probe and into the instrument. As the blood sample flows from the syringe, its volume is replaced by air that passes through an opening in the coupling between the syringe and the instrument, and through an annular space between the probe and the opening of the syringe.

While multiple use instruments that draw blood in this manner may operate satisfactorily in many applications, they present some difficulties. In particular, the sample introduction device, including the inside of the aspiration probe, must be routinely cleaned between samples to prevent clogs and cross contamination of the samples. Although blood gas sample syringes are treated with an anti-coagulant, blood samples often contain micro-clots which can block the narrow flow passages of sample introduction devices of analytical instrumentation. In many current blood gas analyzers, such as the Rapidpoint 400 sold by Bayer Corporation of Medfield, Mass., problems associated with these clots are minimized by providing the inlet of the sample aspiration probe with the smallest diameter of the entire sample flow path through the sample introduction device. If a clog does occur, it is likely to be at the tip of the probe and can be cleared by wiping or flushing. However, the inclusion of probe washing facilities complicates the fluidics of a clinical analyzer. Moreover, the washing sequence is time consuming and disadvantageously reduces the availability of the instrument for sample analysis. Such delay may be particularly disadvantageous in some operating environments such as, for example, in critical care facilities.

Further, discarded wash fluid or reagent comprises a significant portion of the waste generated by such conventional analytical instrumentation. This waste is classified as biohazardous and thus disposal thereof is relatively expensive, both in economic and environmental terms. This waste also poses a potential health risk to health care workers and those who may otherwise come into contact with the waste during or after disposal.

Thus, a need exists for an improved sample introduction device that reduces the need for washing between samples to reduce the amount of reagent required therefor and that otherwise overcomes the drawbacks of the prior art.

SUMMARY OF THE INVENTION

According to an embodiment of the present invention, a sample introduction device is adapted for introducing a sample into a sample chamber of a sensor from a container maintained in fluid communicating relationship therewith. The sample introduction device comprises a probe of substantially tubular construction, having a first end adapted to extend into the container and a second end adapted for connection to a material volume supply. The probe is adapted to inject a predetermined volume of gas into the container to displace a predetermined volume of the sample from the container into the sample chamber.

In a variation of the first aspect of the present invention, a test apparatus is provided for determining analyte content of a sample. The test apparatus comprises the sample introduction device of the first aspect of the invention. In addition, the sensor has at least one sample chamber and the container is adapted for being maintained in fluid communicating relationship therewith.

In a second aspect of the present invention, a method is provided for introducing a sample into a sample chamber. This method comprises the steps of maintaining a sample container in fluid communicating relationship with the sample chamber; and injecting a predetermined volume of gas into the sample container, wherein a predetermined volume of a sample disposed within the sample container is displaced by the gas from the container into the sample chamber.

In a variation of this second aspect of the invention, a method of operating a sensor is provided. This method comprises the steps of introducing a sample into a single use sample chamber as set forth in the second aspect;

measuring predetermined parameters of the sample disposed in the single use sample chamber; and discarding the sensor with sample fluid disposed within the sample chamber.

The above and other features and advantages of this invention will be more readily apparent from a reading of the following detailed description of various aspects of the invention taken in conjunction with the accompanying drawings.

DETAILED DESCRIPTION OF THE PREFERRED EMBODIMENTS

Figure 1:
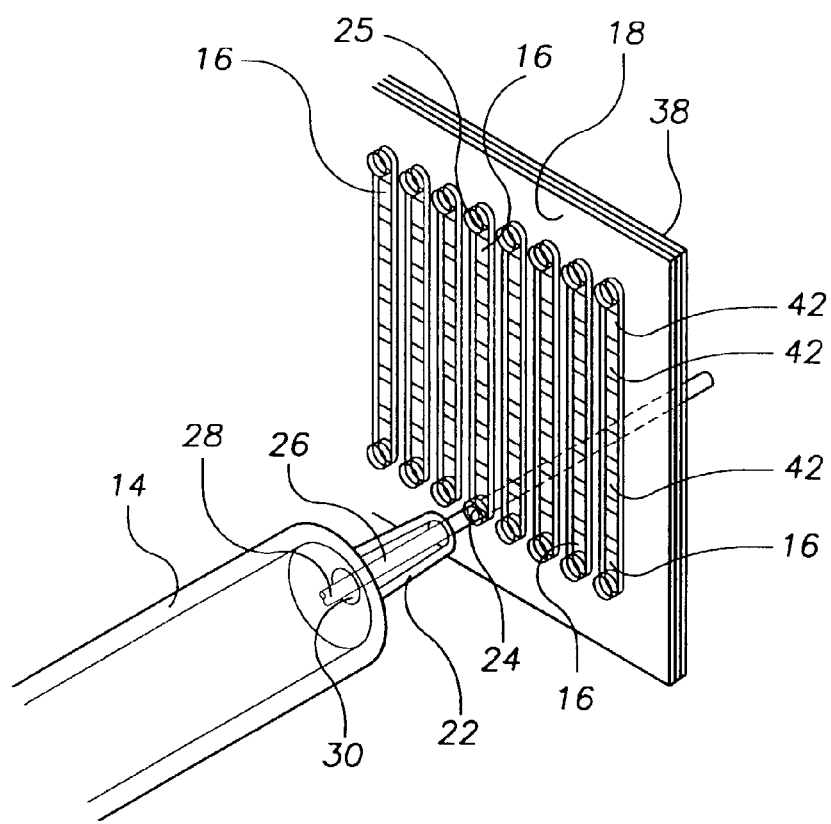
FIG. 1 is a perspective view, with portions thereof in phantom and portions thereof broken away, of a representative application utilizing an embodiment of the present invention.

Referring to the figures set forth in the accompanying Drawings, illustrative embodiments of the present invention will be described in detail hereinbelow. For clarity of exposition, like features shown in the accompanying drawings shall be indicated with like reference numerals and similar features shown for example in alternate embodiments in the drawings, shall be indicated with similar reference numerals.

Briefly described, as shown in the Figs., the present invention includes a sample introduction device 10 (FIG. 2) adapted for introducing a liquid sample or test sample 12 (FIG. 2) from a container or syringe 14 to a sample chamber 116 of a sensor assembly 118 for analysis. Device 10 includes a Luer fitting or coupling 20 (FIG. 2) adapted to mate an outlet 22 of the container in a concentric orientation with an input aperture 24 of the sample chamber. A tubular probe 26 is adapted to extend in fluid tight engagement through backing web 38 of sensor assembly 18 in (FIG. 1) or sensor assembly 118 in (FIG. 2), for concentric placement with both outlet 22 and inlet aperture 24 with a first end 28 thereof extending into the syringe. A distal end 29 is adapted for attachment to an air supply (not shown) as will be discussed hereinafter. Probe 26 has a predetermined diameter sufficient to provide an annular clearance or opening 30 (FIGS. 1, 3 and 6) between the probe and each of outlet 22 and inlet aperture 24. The probe is adapted to inject a predetermined volume of a material 32, preferably a gas such as air (FIGS. 4 and 5) therein. The gas serves to displace a predetermined volume of sample 12 from container 14 through annular clearance 30 to enable the sample to pass therethrough into sample chamber 16 or 116.

The combination of mating syringe 14 directly to sensor assembly 18 or 118 and injecting air into the syringe through probe 26 to displace the sample therefrom, rather than drawing the sample into the probe, serves to advantageously eliminate the need for washing the interior of the probe. Moreover, the use of the present invention in combination with the aforementioned multiple single use sensor assembly 18 or 118 advantageously provides "hands-off" sample introduction, substantially reduces the need for probe and sample chamber washing, to in turn, reduce use of wash reagents.

Sample introduction device 10 of the present invention is suitable for use in many types of analytical instrumentation. It is particularly useful in the critical care environment for the anaerobic withdrawal of small volumes of arterial blood from a sample collection syringe.

Throughout this disclosure, the term "analyte" shall refer to any substance, compound, or characteristic such as, for example, pH, oxygen, carbon dioxide and ions, among others, capable of detection and/or measurement relative to a liquid sample. Similarly, the term "concentration" shall refer to the level or degree to which an analyte is present in a sample. The term "tubular" shall refer to an elongated, hollow member of substantially any transverse cross-sectional geometry, including, but not limited to circular, square or other polygonal geometry.

Turning now to the drawings in detail, in FIG. 1 portions of a sample introduction device 10 (FIG. 2) are shown in a representative application. Sensor assembly 18 includes a series of sample chambers 16, each of which include an input aperture 24 and an output aperture 25. Syringe 14 is disposed in operative engagement with an input aperture 24 of one of the sample chambers 16. Probe 26 is shown in its fully inserted position concentrically disposed with both input aperture 24 and outlet 22 of syringe 14, with first end 28 thereof extending into syringe 14. Luer fitting 20 (FIG. 2), including the fluid pathway between syringe 14 and input aperture 24 of the sample chamber have been omitted from FIG. 1 for clarity.

As also shown, sensor assembly 18 comprises a multiple single use optical sensor of the type disclosed in the above-referenced "OPTICAL SENSOR" patent application. Alternatively, however, the present invention may be utilized in combination with substantially any type of sample chamber, including single and multiple use sample chambers, in addition to the multiple single use chambers shown. In this regard, the present invention may be effectively utilized in combination with sample chambers of various types of sensors in addition to the optical sensors shown, including, for example, chemical, electrical and/or electrochemical sensors.

Figure 2:
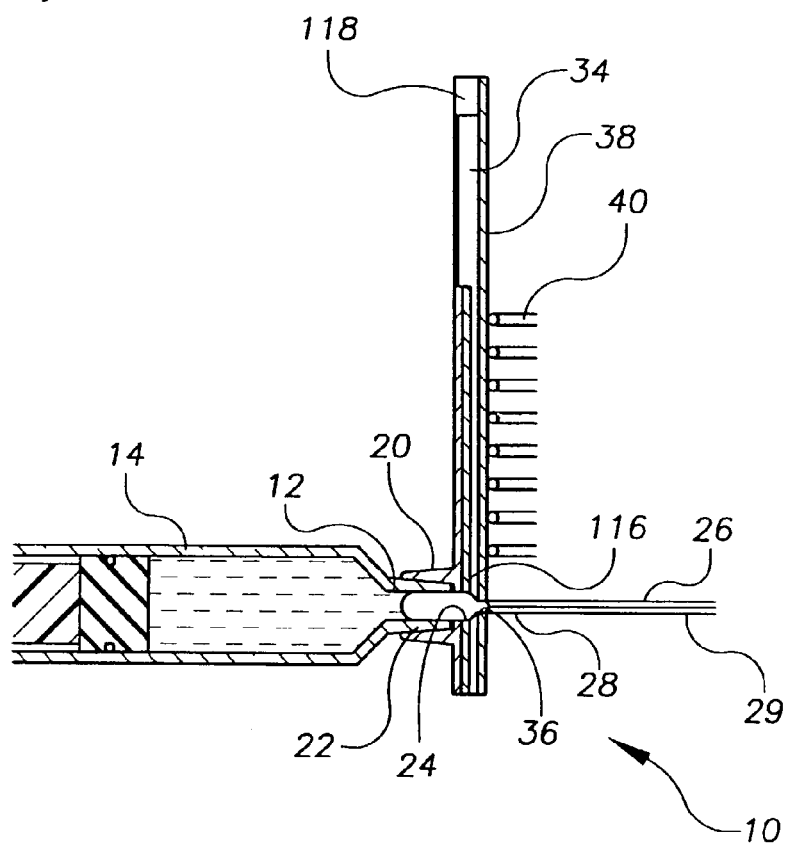
FIG. 2 is a cross-sectional elevational view of an other similar representative application utilizing an embodiment of the present invention, during a step in the operation thereof.

Referring now to FIG. 2, a sample 12, such as, for example, blood, urine or other fluid, is maintained within syringe 14. Outlet 22 of the syringe is matingly engaged with a Luer fitting 20 of substantially conventional construction. Luer fitting 20 is sized and shaped to receive and maintain outlet 22 in fluid communicating relation with input aperture 24 of sample chamber 116. In a preferred embodiment, as shown, the Luer fitting is adapted to provide a fluid tight seal with outlet 22 to prevent leakage of sample 12 during sample introduction as will be discussed hereinafter. As also shown, Luer fitting 20 is preferably disposed integrally with a sensor assembly 118, in concentric alignment with an input aperture 24. Thus, when fully engaged with fitting 20, outlet 22 is preferably maintained in concentric orientation with the input aperture 24.

Sensor assembly 118 is substantially similar to sensor assembly 18 shown in FIG. 1, with the exception that each sample chamber 116 thereof includes an integral waste receptacle 34 which will be discussed in greater detail hereinafter. A probe aperture 36 is disposed concentrically with input aperture 24, on an opposite side of sensor assembly 118 therefrom. Thus, as shown, probe aperture 36 is disposed in substrate or backing web 38 of sensor assembly 118. The probe aperture is sized and shaped to provide a substantially fluid tight seal with probe 26 when inserted therein, as will be discussed hereinafter. Thus, in a preferred embodiment, web 38 is fabricated as a flexible film as disclosed in the above referenced "OPTICAL SENSOR" patent application and probe aperture 36 is sized and shaped to be slightly smaller than, to provide an interference fit with, probe 26 to thus form the fluid tight seal therebetween.

As shown, probe 26 is maintained in a ready or retracted position relative sensor assembly 118 and syringe 14 by a fixture or support means (not shown) of a test apparatus (also not shown) within which the present invention is incorporated. The test apparatus also includes a series of emitter/receptor heads or optical reader heads 40 maintained in alignment with each of a series of sensor stripes 42 (FIG. 1) of the sensor assembly. Emitter/receptor heads 40 are thus adapted to measure response of sensor stripes 42 to the presence of analytes in sample 12 in a manner set forth in the above referenced "OPTICAL SENSOR" patent application, and as will be discussed in greater detail hereinafter with respect to the operation of the present invention. In this regard, moreover, the specific operations of sample introduction device 10, including the operation of emitter/receptor heads 40, operation of probe 26 and the supply of material 32 are preferably controlled by a logic device or control module (not shown) such as a computer incorporated into the test apparatus in a manner familiar to those skilled in the art.

The orientation of sample introduction device 10, as shown, with outlet 22 matingly engaged with fitting 20 and probe 26 in its ready position, comprises an initial step in the operation of the present invention.

Figure 3:
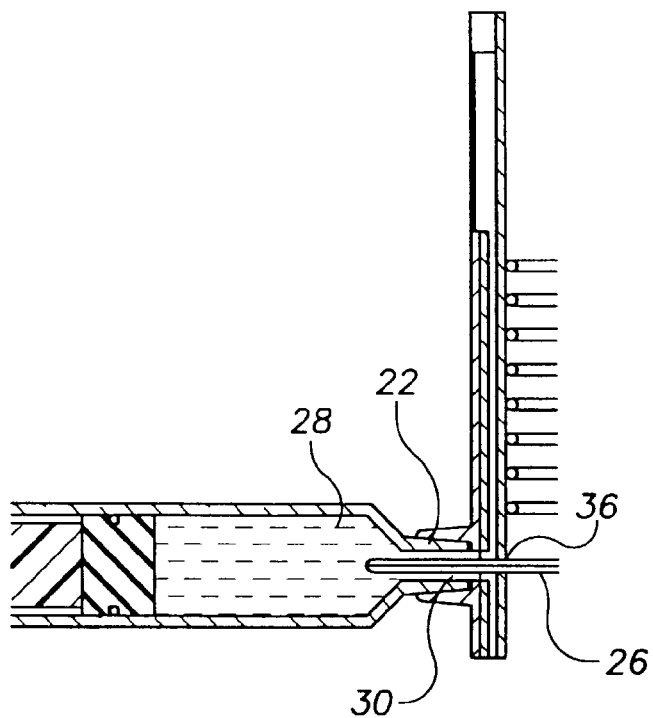
FIG. 3 is a view similar to that of FIG. 2, during another step in the operation of the present invention.

Referring now to FIG. 3, in a subsequent step in the operation of the present invention, probe 26 is inserted into probe aperture 36, input aperture 24 and outlet 22 until first end 28 is disposed within sample 12. As shown, probe 26 is preferably disposed concentrically with apertures 36 and 24, as well as with outlet 22. The volume of the probe inserted therein will displace a predetermined, relatively small volume of sample 12 into annular opening 30 within outlet 22 as shown.

Figure 4:
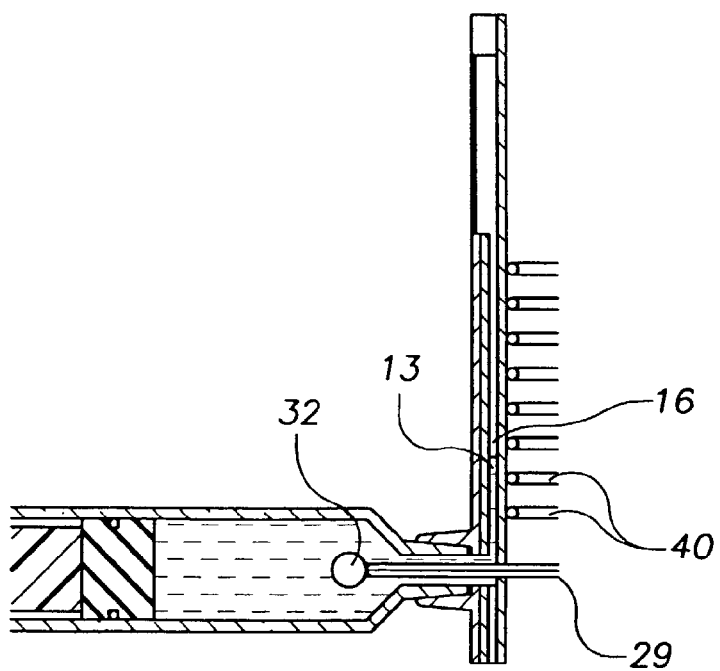
FIG. 4 is a view similar to those of FIGS. 2 and 3, during a further step in the operation of the present invention.

Turning now to FIG. 4, the next step in the operation of the present invention is to supply a predetermined volume of material 32 to distal end 29 of probe 26. Material 32 may be substantially any flowable substance, i.e. an immiscible liquid, a paste-like material such as silicone grease, solid beads or granules, or gas. The particular material selected is preferably inert. As used herein, the term 'inert' is defined as being substantially non-reactive with the sample. Similarly, the term 'inert gas' is defined as a gas that only changes the partial pressure through its fractional equivalence or when it is dissolved in the sample, as opposed to a chemically reactive gas such as a chloride which may rapidly react chemically with elements in the sample to form HCL.

Although a non-reactive material is preferred, one skilled in the art will recognize that non-reactivity with the sample is important only to the degree that sample remaining in the sample container is affected. The sample being analyzed is disposed within the sample chamber and is not in direct contact with the material 32. Thus, if only one sample is to be taken from sample container, a reactive material may be utilized. In the case of a blood sample, the presence of any gas phase, for example, will affect the levels of some analytes (particularly dissolved oxygen). This is a potential problem with any sampling method which draws a sample from a fixed volume. From a practical viewpoint the degradation from an inert bubble such as air in a blood sample is relatively slow, and if the sample is to be used for multiple tests, the air bubbles are preferably expelled from the syringe immediately after sampling.

As discussed hereinabove, material 32 is preferably an inert gas. A particular gas is chosen based on convenience and availability. The gas may comprise any gas which does not affect the sample, or a combination of such gases provided by any convenient gas supply, such as, for example, a commercially available compressed gas canister. In this regard, when the sample is whole blood, examples of suitable gases include air, nitrogen and propane. In a preferred embodiment, the gas comprises air and is provided by either a gas canister or by conventional pump or compressor means (not shown). As shown, once the supply of gas is initiated, a bubble of gas 32 is formed at first end 28 of probe 26. Sample 12 is displaced thereby and as shown, begins to fill sample chamber 116. Optical reader heads 40, or alternatively, additional optical sensors (not shown), detect presence of sample 12 in the sample chamber and also determine the integrity (absence of bubbles) of the sample disposed within the sample chamber.

Figure 5:
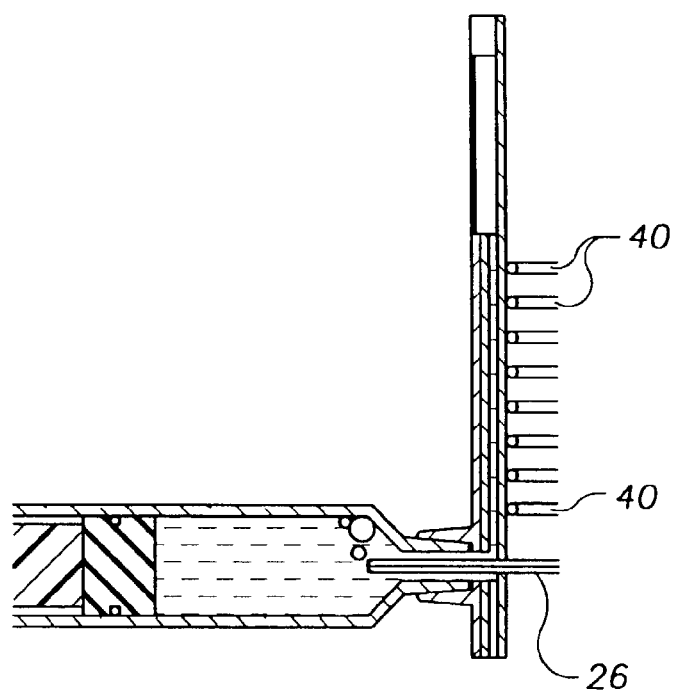
FIG. 5 is a view similar to those of FIGS. 2–4, during a still further step in the operation of the present invention.

As shown in FIG. 5, once reader heads 40 (or the alternative optical sensors) detect sample chamber 116 is substantially filled by sample 12, the supply of gas 32 is terminated. Alternatively, a predetermined fixed volume of gas is injected. Optical reader heads 40 are then operated in the manner set forth in the above-reference "OPTICAL SENSOR" patent application to test, or collect information, such as, for example, analyte concentration within sample 12, from each portion of the sensor stripes 42 (FIG. 1) disposed within sample chamber 116.

Figure 6:
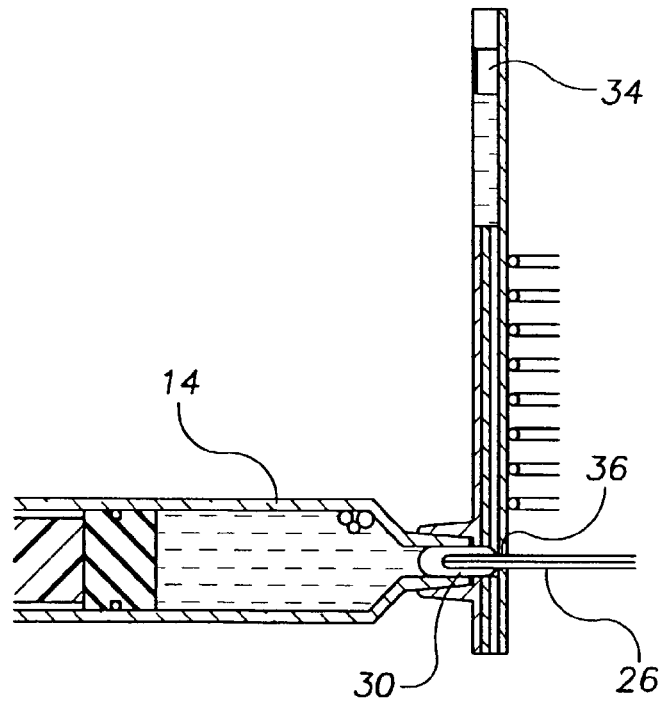
FIG. 6 is a view similar to those of FIGS. 2–5, during a yet further step in the operation of the present invention.

Turning now to FIG. 6, once testing of sample 12 is complete, probe 26 is withdrawn from syringe 14. As the probe moves through probe aperture 36, the aforementioned fluid tight engagement with probe 26 serves to effectively wipe any residual portion of sample 12 from the exterior of the probe. This wiping action advantageously cleans probe 26 without the need to flush the interior thereof with wash reagents, as would otherwise be necessary in the event samples were passed through the interior of the probe as in the aforementioned prior art devices.

In a preferred embodiment as shown, additional gas is supplied to the probe once the probe has been withdrawn from the sample fluid disposed within the syringe, and before first end 28 of the probe is withdrawn from probe aperture 36. This additional gas serves to push sample 12 out of sample chamber 116 and into waste receptacle 34. In this manner, sample 12 may simply remain in the sensor assembly to be discarded along with sensor assembly 118 once all of the sample chambers thereof have been utilized, as will be discussed hereinafter. Alternatively, in the aforementioned embodiment that utilizes a sample chamber 16 (FIG. 1) without a waste receptacle, probe withdrawal may be implemented without the additional supply of gas, to leave sample 12 in the sample chamber. Thus, in both these embodiments, the sample 12 may simply remain in the sensor assembly and be subsequently discarded along with sensor assembly 18 or 118 once all of the sample chambers thereof have been utilized, as will be discussed hereinafter.

In a further alternative, rather than leave sample 12 within the sensor assembly, the aforementioned supply of additional gas may be utilized to push sample 12 out of output aperture 25 (FIG. 1). The sample may then be collected by any suitable collection means (not shown) familiar to those skilled in the art.

The final step in the operation of the present invention is to completely withdraw probe 26 into its ready position as shown in FIG. 2, whereupon syringe 14 may be removed and a fresh sample chamber 16 or 116 indexed into sensing contact with emitter/receptor heads 40 for subsequent testing in the manner described hereinabove.

Thus, as shown and described hereinabove, the present invention serves to effectively reverse the flow path of prior art instrumentation which, as discussed hereinabove, use an aspiration probe to withdraw a blood sample from a syringe. In this manner, rather than removing a sample and letting air be drawn into the syringe to replace the volume of the withdrawn sample, the present invention pumps an air bubble from probe 26 into syringe 14, displacing a volume of blood sample 12, which flows through the syringe/probe annular opening 30, into the instrument Luer coupling 20 and subsequently into sample chamber 16 or 116. The benefit of this mode of operation is that blood does not enter the inside of probe 26, and thus permits cleaning by wiping the exterior of the probe, rather than washing the interior thereof. Advantageously, this aspect serves to reduce time, safety and waste relative to the prior art.

It should be understood that although a gas bubble is used for the displacement volume in the preferred embodiment, any material (e.g. water, a liquid or a flowable paste-like substance such as silicone grease) which can be dispensed through the probe and will displace the sample material, may be used if contamination in re-sampling is not an issue.

Moreover, use of the present invention in combination with a single use sample chamber nominally eliminates the need for sample chamber washing and simplifies disposal since the sample can remain in the sample chamber after testing to be subsequently discarded therewith as a single unit. The present invention thus effectively provides a sample handling system that substantially reduces the need for wash reagent, waste containers to receive the used wash reagent and samples, and time consuming wash sequences.

The foregoing description is intended primarily for purposes of illustration. Although the invention has been shown and described with respect to an exemplary embodiment thereof, it should be understood by those skilled in the art that the foregoing and various other changes, omissions, and additions in the form and detail thereof may be made therein without departing from the spirit and scope of the invention.

Having thus described the invention, what is claimed is:

1. A sample introduction apparatus comprising:
   a sample chamber having an inlet aperture;
   a container, having an outlet disposed in fluid communicating relation with said inlet aperture of the sample chamber;
   a probe of substantially tubular construction, adapted to extend through the inlet aperture and through the outlet into the container;
   said probe having a second end adapted for connection to a supply of material;
   said probe being configured to inject a predetermined volume of the material into the container under sufficient positive pressure to displace a predetermined volume of a sample from the container into the sample chamber; and
   said probe being sized and shaped to provide clearance between said probe and each of the inlet aperture and outlet sufficient to enable said predetermined volume of the sample to be displaced from the container into the sample chamber therethrough;
   wherein interior probe surfaces remain free of the sample.

2. The sample introduction device as set forth in claim 1, wherein said probe is substantially cylindrical and is adapted for disposition concentrically within the outlet and the inlet aperture, said clearance being substantially annular.

3. The sample introduction device as set forth in claim 1, wherein said probe is adapted to extend in fluid tight engagement through a probe aperture disposed in a wall of the sample chamber concentrically with said inlet aperture.

4. The sample introduction device as set forth in claim 1, wherein said probe is substantially cylindrical and is adapted for simultaneous disposition within the outlet and the inlet aperture.

5. The sample introduction device as set forth in claim 1, further comprising a fitting adapted to mate the outlet of the container in fluid communicating relationship with the inlet aperture of the sample chamber.

6. The sample introduction device as set forth in claim 5, wherein said fitting is adapted to maintain the outlet of the container in physical contact with the sample chamber.

7. The sample introduction device as set forth in claim 6, wherein said fitting is integrally fastened to the sample chamber.

8. The sample introduction apparatus as set forth in claim 1, wherein said material is selected from the group consisting of a liquid, a paste, solid beads or granules, or gas.

9. The sample introduction apparatus as set forth in claim 8, wherein said material is chemically inert.

10. The sample introduction apparatus as set forth in claim 1, wherein said material comprises air.

11. A sample introduction apparatus comprising:
   a sample chamber;
   a container disposed in fluid communicating relationship with said sample chamber; and
   a probe of substantially tubular construction, having a first end adapted to extend into said container, and having a second end adapted for connection to a supply of material; and
   said probe being configured to inject a predetermined volume of the material into said container under sufficient positive pressure to displace a predetermined volume of the sample from the container into said sample chamber;
   wherein interior probe surfaces remain free of the sample.

* * * * *